United States Patent
Dickerson

(10) Patent No.: US 8,623,093 B2
(45) Date of Patent: Jan. 7, 2014

(54) SLEEVE FOR MODULAR REVISION HIP STEM

(75) Inventor: Jeffrey Paul Dickerson, Warsaw, IN (US)

(73) Assignee: Zimmer, Inc., Warsaw, IN (US)

(*) Notice: Subject to any disclaimer, the term of this patent is extended or adjusted under 35 U.S.C. 154(b) by 27 days.

(21) Appl. No.: 13/161,125

(22) Filed: Jun. 15, 2011

(65) Prior Publication Data

US 2012/0010720 A1 Jan. 12, 2012

Related U.S. Application Data

(60) Provisional application No. 61/362,006, filed on Jul. 7, 2010.

(51) Int. Cl.
*A61F 2/32* (2006.01)
(52) U.S. Cl.
USPC .................. 623/22.42; 623/19.11; 623/19.13; 623/22.4
(58) Field of Classification Search
USPC ............ 623/22.4–22.42, 23.23, 23.31, 23.42, 623/23.46
See application file for complete search history.

(56) References Cited

U.S. PATENT DOCUMENTS

| | | | |
|---|---|---|---|
| 2,934,065 A | 4/1960 | Townley | |
| 4,536,894 A | 8/1985 | Galante et al. | |
| 5,002,578 A | 3/1991 | Luman | |
| 5,080,685 A | 1/1992 | Bolesky et al. | |
| 5,507,829 A | 4/1996 | Thongpreda et al. | |
| 6,863,690 B2 * | 3/2005 | Ball et al. | 623/19.11 |
| 6,863,692 B2 | 3/2005 | Meulink | |
| 7,044,975 B2 | 5/2006 | Cheal et al. | |
| 7,135,044 B2 | 11/2006 | Bassik et al. | |
| 7,175,664 B1 * | 2/2007 | Lakin | 623/19.14 |
| 7,435,263 B2 | 10/2008 | Barnett et al. | |
| 7,455,695 B2 | 11/2008 | Khalili et al. | |
| 7,575,603 B2 | 8/2009 | Bergin et al. | |
| 7,766,968 B2 | 8/2010 | Sweeney | |
| 7,776,098 B2 | 8/2010 | Murphy | |
| 7,828,805 B2 | 11/2010 | Hoag et al. | |
| 2004/0010319 A1 | 1/2004 | McTighe et al. | |
| 2005/0004679 A1 | 1/2005 | Sederholm et al. | |
| 2005/0143835 A1 | 6/2005 | Gilbertson | |
| 2005/0234559 A1 | 10/2005 | Fernandez et al. | |
| 2007/0043446 A1 | 2/2007 | Murray | |
| 2007/0043448 A1 | 2/2007 | Murray | |
| 2007/0078516 A1 * | 4/2007 | Emami | 623/19.14 |
| 2007/0118229 A1 | 5/2007 | Bergin et al. | |
| 2007/0173945 A1 | 7/2007 | Wiley et al. | |

(Continued)

OTHER PUBLICATIONS

Article: Femoral Revision: The Role of Modular Femoral Components, Fares Hadded et al., Ortho Supersite, accessed Apr. 20, 2010.

(Continued)

*Primary Examiner* — Bruce E Snow
*Assistant Examiner* — Brian Dukert
(74) *Attorney, Agent, or Firm* — Schwegman, Lundberg & Woessner P.A.

(57) ABSTRACT

The present disclosure provides a femoral prosthesis for use during a revision procedure. The femoral prosthesis includes a body, a neck, a stem, and a sleeve. The sleeve facilitates reattachment of an osteotomized proximal femur, specifically the greater trochanter, following a revision femoral prosthesis surgery involving an extended trochanteric osteotomy. Additionally, the sleeve promotes ingrowth of the osteotomized proximal femur with the sleeve.

20 Claims, 10 Drawing Sheets

(56) References Cited

U.S. PATENT DOCUMENTS

| | | |
|---|---|---|
| 2007/0179630 A1 | 8/2007 | Benedict et al. |
| 2008/0140210 A1 | 6/2008 | Doubler et al. |
| 2008/0140211 A1 | 6/2008 | Doubler et al. |
| 2008/0281428 A1* | 11/2008 | Meyers et al. ............. 623/20.35 |
| 2008/0281430 A1 | 11/2008 | Kelman et al. |
| 2009/0048603 A1 | 2/2009 | Hoag et al. |
| 2009/0076620 A1 | 3/2009 | Khalili et al. |
| 2009/0164026 A1 | 6/2009 | Mikami et al. |
| 2009/0270996 A1 | 10/2009 | Meulink et al. |
| 2010/0114324 A1 | 5/2010 | Gibbs et al. |
| 2011/0009973 A1 | 1/2011 | Meyers et al. |

OTHER PUBLICATIONS

Product Brochure—ZMR Hip System, 19 pages, Zimmer, Inc., 2004, 2008, 2009.

* cited by examiner

SLEEVE FOR MODULAR REVISION HIP STEM

CROSS REFERENCE TO RELATED APPLICATION

This application claims priority to U.S. Provisional Patent Application Ser. No. 61/362,006, entitled "SLEEVE FOR MODULAR REVISION HIP STEM," filed Jul. 7, 2010, the disclosure of which is hereby expressly incorporated by reference herein in its entirety.

BACKGROUND

1. Field of the Disclosure

The present disclosure relates to a femoral prosthesis. More particularly, the present disclosure relates to a femoral prosthesis for use during a revision procedure, the femoral prosthesis including a sleeve to facilitate reattachment of the greater trochanter.

2. Description of the Related Art

An orthopaedic prosthesis may be used to replace some or all of a patient's hip joint in order to restore use of the hip joint following a traumatic injury or deterioration due to aging or illness, for example. A femoral prosthesis having a stem, a neck, and a head may be used to replace a portion of the patient's femur and an acetabular prosthesis may be used to replace a portion of the patient's acetabulum.

If problems develop with an original or primary prosthesis over time, the original prosthesis may need to be removed and replaced with a new prosthesis, a procedure known as a revision procedure. A revision procedure may be necessary if an infection develops around the original prosthesis, if the original prosthesis experiences excessive wear or damage, or if the original prosthesis begins to loosen in the patient's bone due to deterioration of the patient's bone around the original prosthesis, for example.

During a revision procedure of the hip joint, for example, it may be necessary to remove an original or primary femoral prosthesis and replace the original femoral prosthesis with a revision femoral prosthesis. As part of the removal of the original femoral prosthesis, in order to obtain access to the original femoral prosthesis, a surgeon may need to perform an extended trochanteric osteotomy (ETO). An ETO procedure typically involves temporary removal of a portion of the proximal femur including the greater trochanter. Upon completion of the original femoral prosthesis removal, the surgeon implants the revision femoral prosthesis and reattaches the portion of the proximal femur osteotomized during the ETO procedure. The surgeon may, in order to reattach the osteotomized proximal femur, wrap cables or sutures around the proximal femur. However, the greater trochanter may remain exposed superior to the remainder of the proximal femur. Such exposure of the greater trochanter may lead to potential loosening of the revision femoral prosthesis and/or degradation of the reattachment of the osteotomized proximal femur.

SUMMARY

The present disclosure provides a femoral prosthesis for use during a revision procedure. The femoral prosthesis includes a body, a neck, a stem, and a sleeve. The sleeve facilitates reattachment of an osteotomized proximal femur, specifically the greater trochanter, following a revision femoral prosthesis surgery involving an extended trochanteric osteotomy. Additionally, the sleeve promotes ingrowth of the osteotomized proximal femur with the sleeve.

According to an embodiment of the present disclosure, a femoral prosthesis having a proximal end and a distal end and configured for implantation in a patient's proximal femur is provided. The femoral prosthesis comprises a proximal body located toward the proximal end of the femoral prosthesis; a neck coupled to the proximal body and extending medially from the proximal body; a distal stem located at the distal end of the femoral prosthesis; and a sleeve couplable to the proximal body. The sleeve includes a plurality of apertures and includes a lateral exterior surface, at least a portion of the lateral exterior surface being positioned laterally and proximally to the proximal body.

According to another embodiment of the present disclosure, a method of implanting a femoral prosthesis into a proximal femur of a patient is provided. The femoral prosthesis includes a proximal body having a neck extending medially and proximally from the proximal body, a distal stem coupled to the proximal body, and a sleeve coupled to the proximal body and having a lateral exterior surface and at least a first and a second aperture. The method comprises the steps of: osteotomizing a portion of the proximal femur of the patient; and implanting the femoral prosthesis such that the distal stem is substantially disposed within the proximal femur of the patient and such that a portion of the lateral exterior surface of the sleeve is positioned laterally and proximally to the proximal body; and attaching the osteotomized portion of the proximal femur to the lateral exterior surface of the sleeve.

According to yet another embodiment of the present disclosure, a femoral prosthesis having a proximal end and a distal end and configured for implantation in a patient's proximal femur is provided. The femoral prosthesis comprises: a proximal body located toward the proximal end of the femoral prosthesis; a neck coupled to the proximal body, the neck extending medially from the proximal body; a distal stem located at the distal end of the femoral prosthesis; and a sleeve having a lateral exterior surface, an anterior flange, a posterior flange, and a plurality of apertures. A portion of the lateral exterior surface comprises a porous surface and the anterior flange is spaced anteriorly to the porous surface of the lateral exterior surface and the posterior flange is spaced posteriorly to the porous surface of the lateral exterior surface.

BRIEF DESCRIPTION OF THE DRAWINGS

The above-mentioned and other features and advantages of this disclosure, and the manner of attaining them, will become more apparent and the disclosure itself will be better understood by reference to the following description of embodiments of the disclosure taken in conjunction with the accompanying drawings, wherein.

Corresponding reference characters indicate corresponding parts throughout the several views. The exemplifications set out herein illustrate exemplary embodiments of the disclosure and such exemplifications are not to be construed as limiting the scope of the disclosure in any manner.

DETAILED DESCRIPTION

Figure 1A:
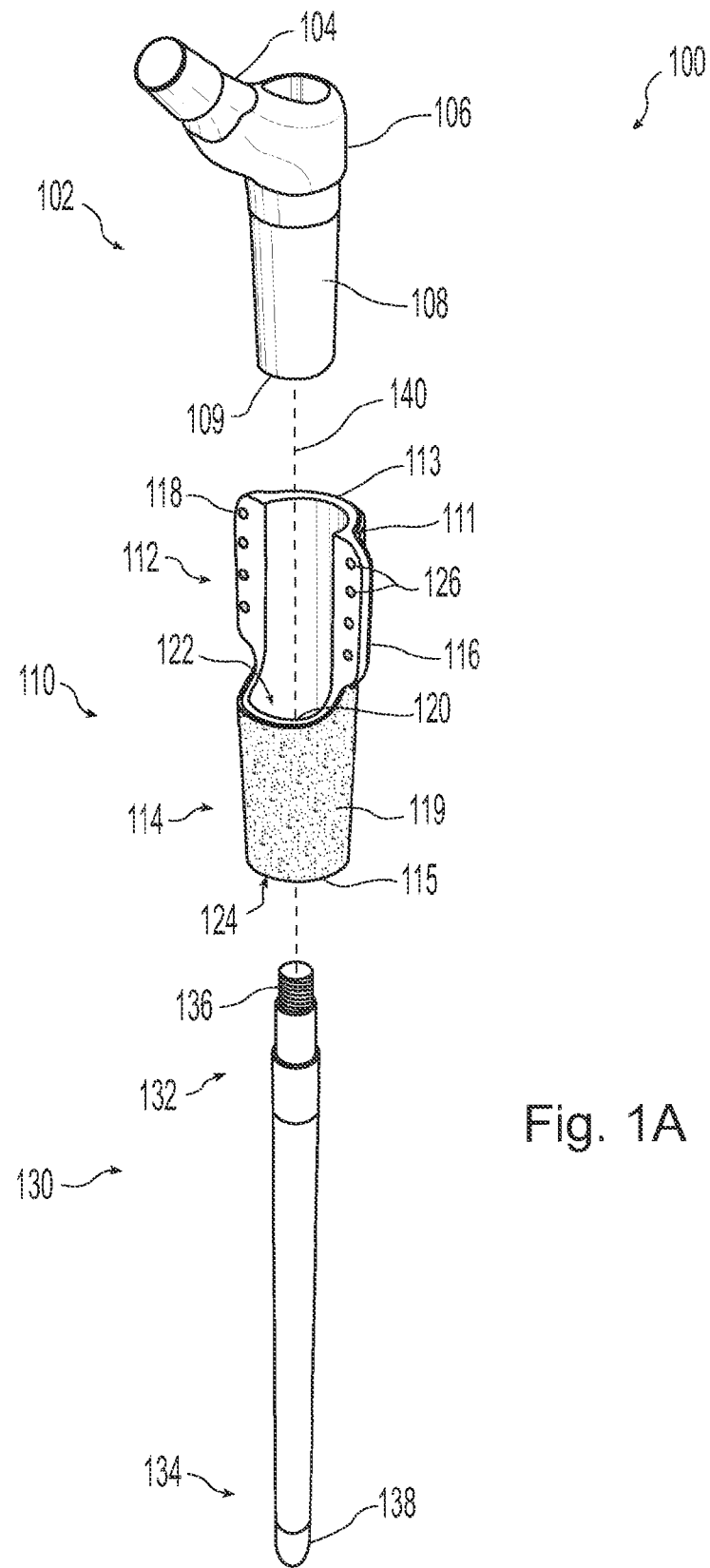
FIG. 1A is an exploded perspective view of an exemplary revision femoral prosthesis of the present disclosure including a neck, a proximal body, a sleeve, and a stem.
Figure 2:
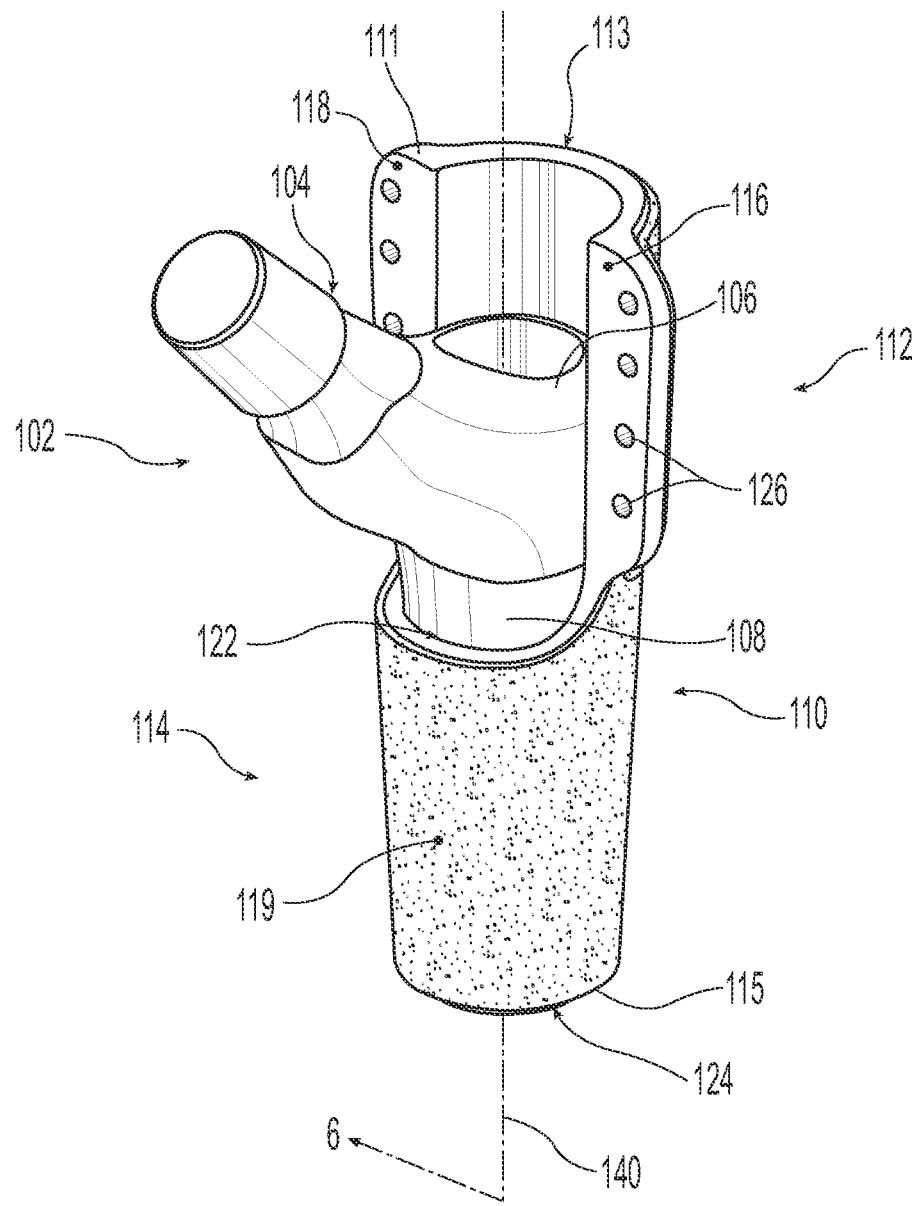
FIG. 2 is a medial perspective view of the neck, the body, and the sleeve of the revision femoral prosthesis of FIG. 1A.

Referring to FIG. 1A, an exemplary revision femoral prosthesis 100 is illustrated including proximal body 102, sleeve 110, and distal stem 130. Upon assembly of prosthesis 100, as shown in FIG. 2, proximal body 102 is disposed substantially within sleeve 110. As shown in FIG. 1A, proximal body 102 is also couplable to distal stem 130. As described and exemplified herein, prosthesis 100 may be used to replace an original or primary femoral prosthesis that has been removed from a proximal femur of a patient for various reasons.

Figure 7A:
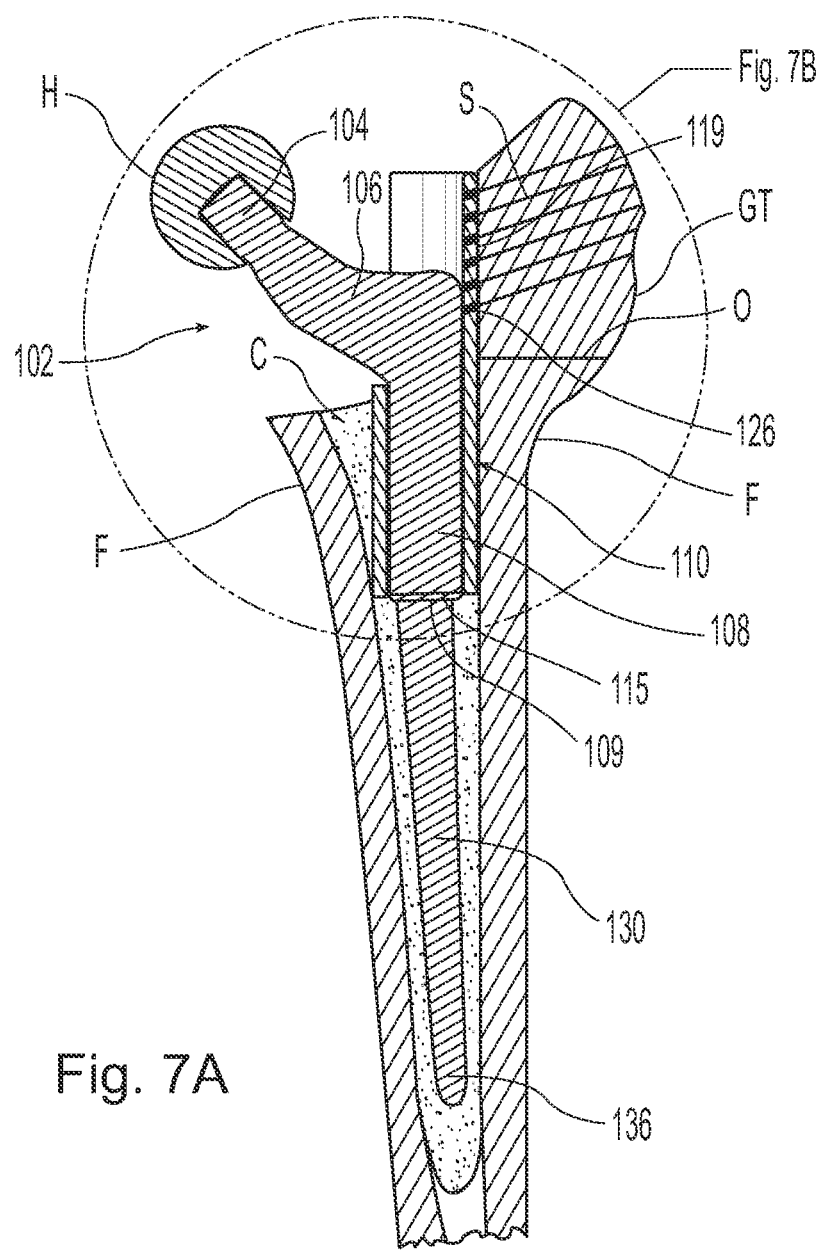
FIG. 7A is a cross-sectional view similar to FIG. 6, also showing the revision femoral prosthesis implanted in a femur and a head coupled to the revision femoral prosthesis.

Referring to FIG. 1A, the illustrative prosthesis 100 shows proximal body 102 having neck 104, proximal portion 106, distal portion 108, and distal end 109. As shown, neck 104 extends medially and proximally (for example, at approximately a 135° angle) from proximal portion 106 and distal portion 108. As shown in FIG. 7A, neck 104 is configured to receive head H which will articulate with the patient's natural acetabulum or a prosthetic acetabular component. Embodiments of the present disclosure also include neck 104 being rigidly affixed to, or integral with, proximal portion 106 of proximal body 102. Additional embodiments of the present disclosure include neck 104 comprising a modular component receivable within proximal portion 106 of proximal body 102, as described in U.S. patent application Ser. No. 13/025,827, entitled "MODULAR REVISION FEMORAL PROSTHESIS," filed Feb. 11, 2011, the disclosure of which is hereby expressly incorporated by reference herein in its entirety. It should also be understood that neck 104 may comprise varying lengths and extension angles, as well as varying anteversion and offset dimensions for desired cooperation with the patient's natural acetabulum or the prosthetic acetabular component, as described in the above-incorporated U.S. patent application Ser. No. 13/025,827.

Figure 1D:
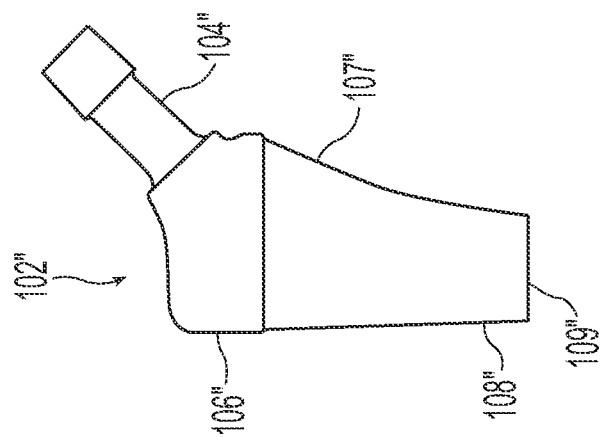
FIG. 1D is yet another elevational view of yet another embodiment of a body and a neck.
Figure 1C:
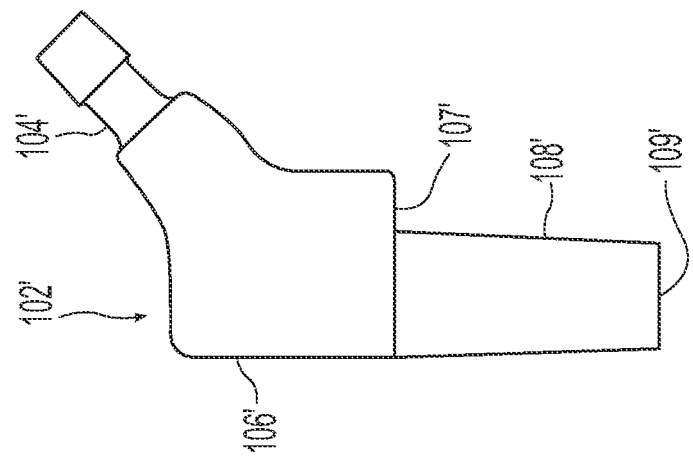
FIG. 1C is an elevational view of another embodiment of a body and a neck.
Figure 1B:
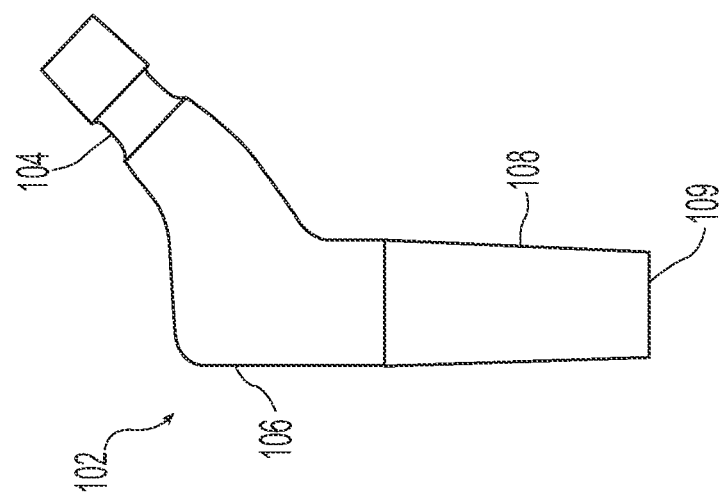
FIG. 1B is an elevational view of the body and the neck of FIG. 1A.

With reference to FIGS. 1B, 1C, and 1D, the surgeon may select a desired proximal body from a set of various proximal bodies 102, 102', 102" that differ in shape and/or size. For example, proximal body 102' shown in FIG. 1C comprises a medial protrusion 107' distal to neck 104' which may aid in resisting subsidence of the proximal femur. FIG. 1D shows an exemplary embodiment of proximal body 102" smaller in size than the embodiments shown in FIGS. 1B and 1C and comprising a medial protrusion 107" also distal to the neck 104". The embodiment of proximal body 102" exemplified in FIG. 1D may be preferred when a patient has relatively minimal bone deficiencies. Proximal bodies 102, 102', 102" may be available in varying sizes, such that the selected proximal body may extend along as little as 20%, 25%, or 30% of the length of prosthesis 100, or along as much as 35%, 40%, or 45% of the length of prosthesis 100, or within any range delimited by any pair of the foregoing values.

Figure 4:
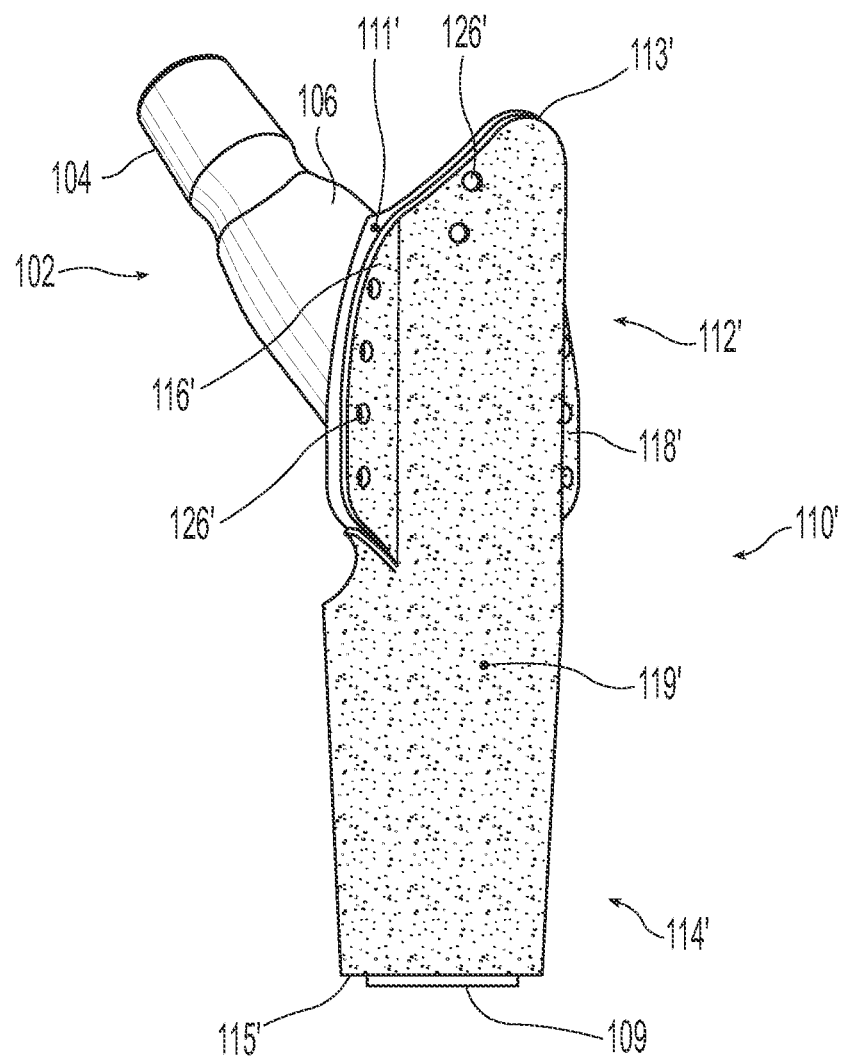
FIG. 4 is an anterior perspective view of the neck, the body, and the sleeve of the revision femoral prosthesis of FIG. 3.

Exemplary embodiments of the present disclosure include at least a portion of proximal body 102 having a porous outer surface. For example, portions of proximal body 102 not disposed within sleeve 110, such as neck 104 and proximal portion 106 (FIGS. 4 and 6), may be plasma sprayed or grit blasted circumferentially to create an outer porous layer. Further, it is within the scope of the present disclosure that at least a portion of proximal body 102 may be constructed of the highly porous biomaterial described in further detail below, and as is also described in the above-incorporated U.S. patent application Ser. No. 13/025,827. Embodiments of the present disclosure having at least a portion of proximal body 102 including a porous outer layer may promote bone and tissue ingrowth when prosthesis 100 is implanted into the patient's femoral canal.

Figure 3:
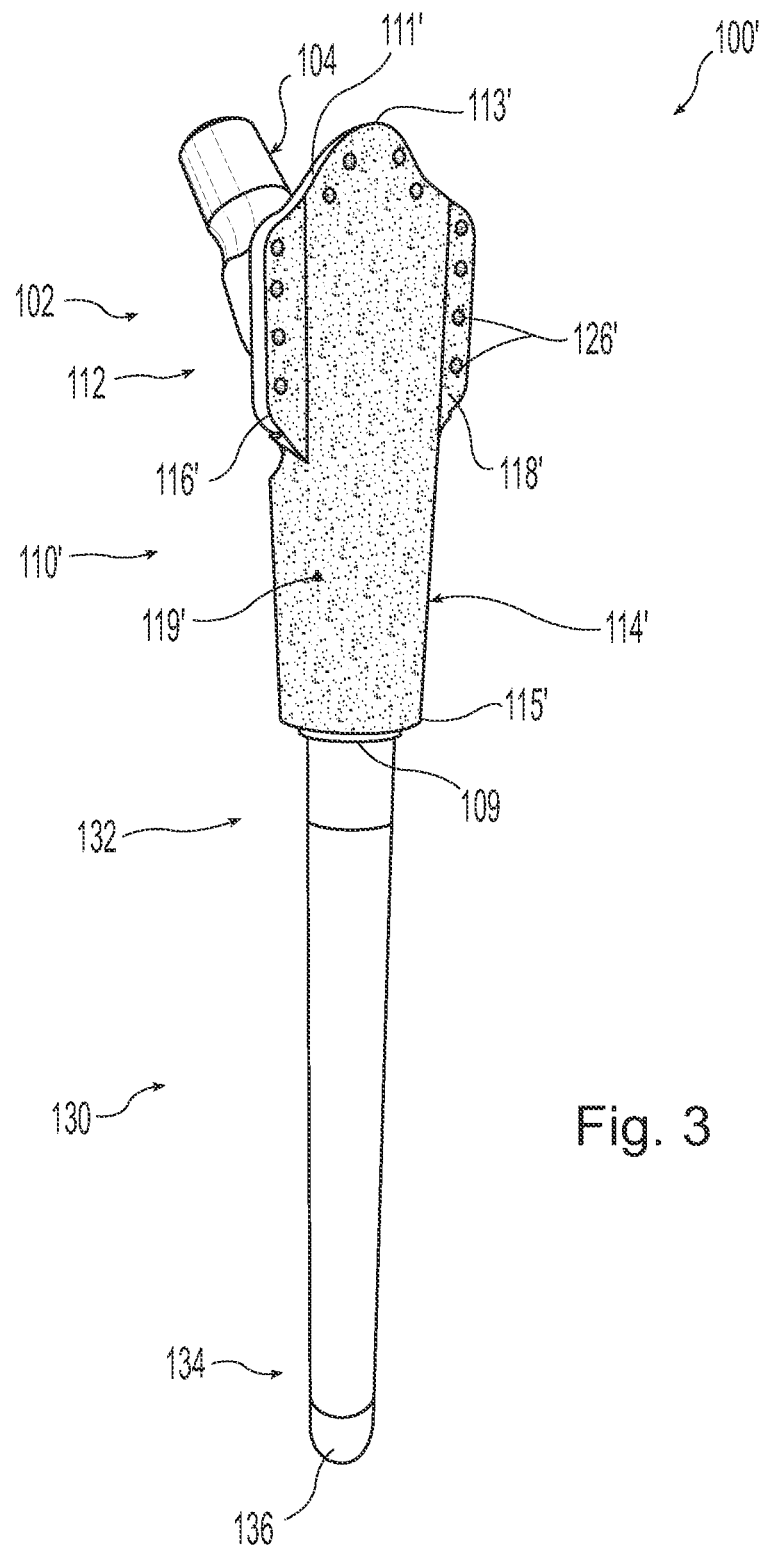
FIG. 3 is a lateral perspective view of another exemplary femoral prosthesis of the present disclosure including a neck, a proximal body, and a stem.
Figure 6:
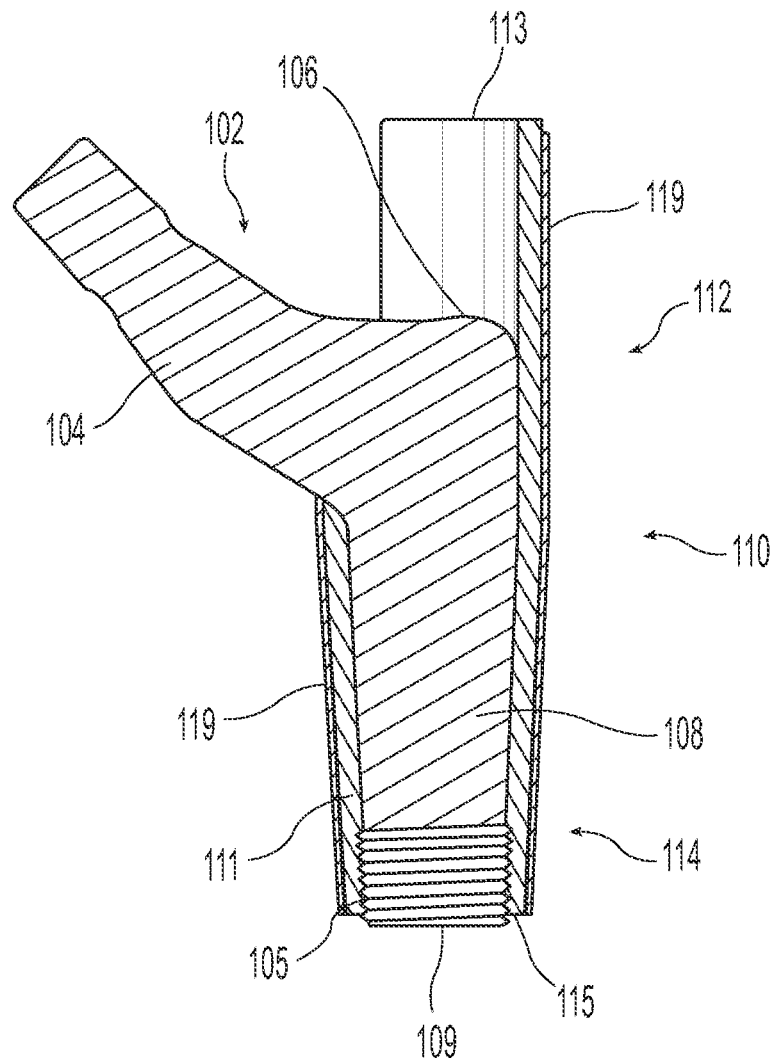
FIG. 6 is a cross-sectional view of the neck, the body, and the sleeve of the revision femoral prosthesis of FIG. 2 taken along line 6 of FIG. 2.

Referring to FIG. 3, distal portion 108 (FIG. 1A) of proximal body 102 is shown disposed within sleeve 110. Exemplary embodiments of proximal body 102 include distal portion 108 having a tapered shape (see, for example, FIG. 1A). In other embodiments of proximal body 102, distal portion 108 may comprise a substantially uniform size and shape throughout. Additionally, assembled prosthesis 100 may include distal portion 108 fully disposed within sleeve 110. As shown in FIG. 6, distal end 109 of proximal body 102 may extend completely through sleeve 110, such that distal end 109 is disposed distal to distal region 114 of sleeve 110.

Referring again to FIG. 1A, sleeve 110 includes body 111 having proximal region 112, proximal end 113, distal region 114, distal end 115, anterior flange 116, posterior flange 118, and exterior surface 119. Sleeve 110 also defines cavity 120 which comprises proximal opening 122 and distal opening 124. It is within the scope of the present disclosure that variations in the shape of sleeve 110 are possible. By way of example, anterior and posterior flanges 116', 118' of sleeve 110' shown in the illustrative embodiment of FIG. 5 each define a rounded trapezoidal shape within a common vertical plane, whereas anterior and posterior flanges 116, 118 in the illustrative embodiment of FIG. 1A each define a rounded rectangular shape within a common vertical plane.

Figure 5:
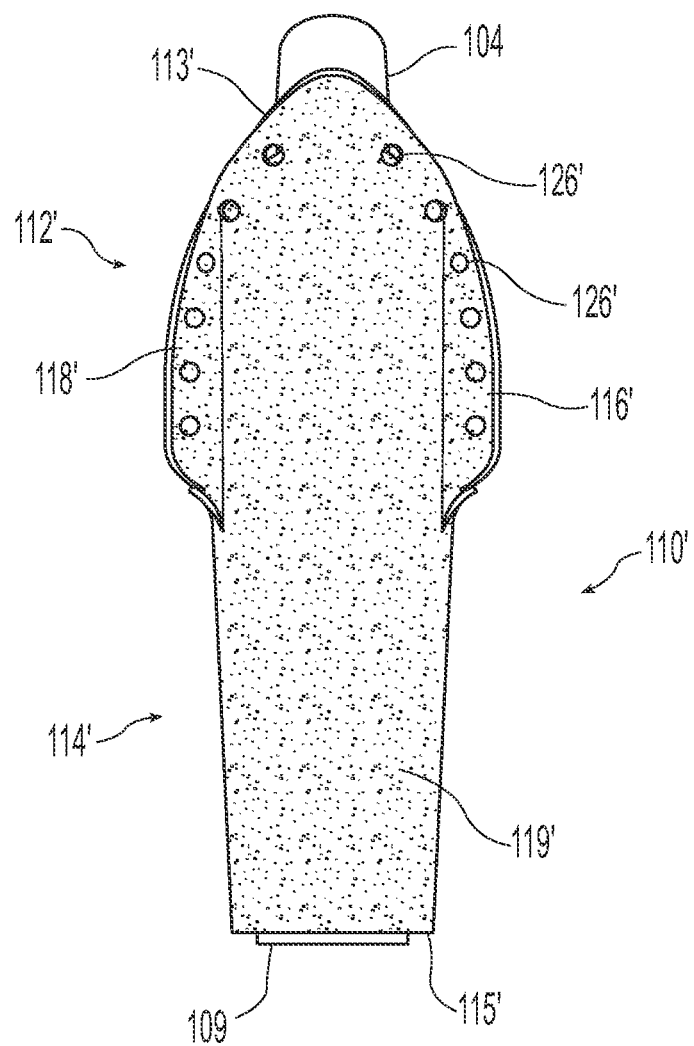
FIG. 5 is a lateral elevational view of the neck, the body, and the sleeve of the revision femoral prosthesis of FIG. 3.

Further, the illustrative embodiment of sleeve 110 shown in FIG. 1A includes proximal end 113 extending linearly along a horizontal plane between anterior and posterior flanges 116, 118, the horizontal plane being perpendicular to axis 140. By contrast, proximal end 113' in the illustrative embodiment of FIG. 5 extends proximally in a substantially rounded or curved manner along axis 140 (FIG. 1A) between anterior and posterior flanges 116', 118'. A rounded proximal end 113', as illustrated in FIG. 5, may provide a desired contour for attachment of soft tissue and/or attaching an osteotomized greater trochanter to exterior surface 119' of sleeve 110' and may also allow for an increased range of motion at the patient's hip joint.

Also, the illustrative embodiment of sleeve 110 shown in FIG. 1A includes cavity 120, defined by the distal region 114 of sleeve 110, which is sized to receive distal portion 108 of proximal body 102. In exemplary embodiments of sleeve 110, cavity 120 may be tapered such that proximal opening 122 is wider that distal opening 124. Embodiments of sleeve 110 may also include cavity 120 having a substantially uniform size throughout. It is also within the scope of the present disclosure that cavity 120 may comprise any of a substantially circular, square, or rectangular shape, wherein the shape of cavity 120 corresponds to the shape of distal portion 108 of proximal body 102.

Referring to the illustrative embodiment of sleeve 110 shown in FIG. 2, proximal body 102 is disposed within sleeve 110. As shown, when proximal body 102 is disposed within sleeve 110, proximal portion 106 of proximal body 102 is positioned medial and distal to the proximal-most portions of exterior surface 119 of sleeve 110. However, in some embodiments of the present disclosure, the proximal-most portions of neck 104 may extend proximally to the proximal-most portions of exterior surface 119 of sleeve 110. See, for example, FIG. 4, where neck 104 extends proximally to the proximal-most portions of exterior surface 119' of sleeve 110'.

With reference to the illustrative embodiments of sleeve 110 depicted in FIG. 2, anterior and posterior flanges 116, 118 are positioned at the anterior and posterior areas of proximal region 112. As shown, anterior and posterior flanges 116, 118 and portions of exterior surface 119 of proximal region 112 may include a plurality of apertures 126. Following implantation of an assembled prosthesis 100, a surgeon may attach one or more surgical fasteners to apertures 126 for securing an osteotomized tissue between the surgical fastener and exterior surface 119 of sleeve 110. FIG. 7A shows an illustrative embodiment of prosthesis 100, implanted in the femur F of a patient. As shown in FIG. 7A, a surgeon may thread a surgical suture, cable, tape, or the like between apertures 126 of the anterior and posterior flanges 116, 118, thereby securing the greater trochanter GT (osteotomized from the proximal femur F at line O), for example, against the lateral and proximal portion of exterior surface 119 of sleeve 110.

Illustrative embodiments of sleeve 110 in which the number of apertures 126 included within anterior and posterior flanges 116, 118, as well as exterior surface 119 of proximal region 112, vary are within the scope of the present disclosure and the number of apertures 126 of sleeve 110 is not intended to be limited to the number depicted herein. For example, FIG. 2 shows an embodiment of sleeve 110 wherein anterior and posterior flanges 116, 118 include four apertures 126 and proximal region 112 includes no apertures 126. Another embodiment of sleeve 110', shown in FIGS. 3 and 4, includes anterior and posterior flanges 116', 118' including three apertures 126' and proximal region 112' including four apertures 126'. As such, it should be understood that the number of apertures 126 defined by anterior and posterior flanges 116, 118 and exterior surface 119 of sleeve 110 may vary.

Referring to FIG. 2, it is within the scope of the present disclosure that body 111 of sleeve 110 may comprise a biocompatible metal, such as titanium, a titanium alloy, cobalt chromium, cobalt chromium molybdenum, tantalum, or a tantalum alloy. According to an illustrative embodiment of the present disclosure, body 111 may comprise a Ti-6A1-4V ELI alloy, such as Tivanium® Alloy which is available from Zimmer, Inc., of Warsaw, Ind. Tivanium® is a registered trademark of Zimmer, Inc. Exterior surface 119 of sleeve 110 may also comprise a biocompatible metal, such as titanium, a titanium alloy, cobalt chromium, cobalt chromium molybdenum, tantalum, or a tantalum alloy.

At least a portion of exterior surface 119 of sleeve 110 may be porous. Because exterior surface 119 defines at least a portion of the bone-contacting surface of sleeve 110, bone and/or soft tissue of the patient's proximal femur, including the greater trochanter, may grow into exterior surface 119 over time to enhance the fixation (i.e., osseointegration) between sleeve 110 and the patient's proximal femur. In some exemplary embodiments of the present disclosure the entire exterior surface 119 of sleeve 110 may be porous. In other embodiments within the scope of the present disclosure only portions of exterior surface 119 within proximal region 112 of sleeve 110 may be porous. According to embodiments of the present disclosure, exterior surface 119 of sleeve 110 may be plasma sprayed circumferentially to create an outer porous layer or grit blasted circumferentially to form a corundumized outer layer of exterior surface 119.

Additionally, exterior surface 119 may be in the form of a fiber metal pad or a sintered metal layer, such as a CSTi™, Cancellous-Structured Titanium™ coating or layer, for example. CSTi™ porous layers are manufactured by Zimmer, Inc., of Warsaw, Ind. CSTi™ is a trademark of Zimmer, Inc. When assembled prosthesis 100 is implanted (FIG. 7A), the porous layer of exterior surface 119 may promote bone and/or tissue ingrowth, as well as facilitate reattachment of osteotomized bone such as an osteotomized greater trochanter GT.

It is also within the scope of the present disclosure that sleeve 110 and/or exterior surface 119 of sleeve 110 may be comprised of a highly porous biomaterial. A highly porous biomaterial is useful as a bone substitute and as cell and tissue receptive material. A highly porous biomaterial may have a porosity as low as 55%, 65%, or 75% or as high as 80%, 85%, or 90%. An example of such a material is produced using Trabecular Metal™ Technology generally available from Zimmer, Inc., of Warsaw, Ind. Trabecular Metal™ is a trademark of Zimmer, Inc. Such a material may be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861, the disclosure of which is expressly incorporated herein by reference. In addition to tantalum, other metals such as niobium, or alloys of tantalum and niobium with one another or with other metals may also be used.

Generally, the porous tantalum structure includes a large plurality of ligaments defining open spaces therebetween, with each ligament generally including a carbon core covered by a thin film of metal such as tantalum, for example. The open spaces between the ligaments form a matrix of continuous channels having no dead ends, such that growth of bone through the porous tantalum structure is uninhibited. The porous tantalum may include up to 75%-85% or more void space therein. Thus, porous tantalum is a lightweight, strong porous structure which is substantially uniform and consistent in composition, and closely resembles the structure of natural bone, such as natural cancellous bone, thereby providing a matrix into which soft tissue and/or bone may grow. According to exemplary embodiments of prosthesis 100, a portion of exterior surface 119 may comprise porous tantalum which provides a matrix into which the bone tissue of the osteotomized greater trochanter may grow, thereby providing fixation of the osteotomized greater trochanter to the implanted sleeve 110.

The porous tantalum structure may be made in a variety of densities in order to selectively tailor the structure for particular applications. In particular, as discussed in the above-incorporated U.S. Pat. No. 5,282,861, the porous tantalum may be fabricated to virtually any desired porosity and pore size, and can thus be matched with the surrounding natural bone in order to provide an improved matrix for bone ingrowth and mineralization.

According to further exemplary embodiments of the present disclosure, porous portions of exterior surface 119 may be impregnated with and/or coated with biologically active agents. Suitable biologically active agents include, for example, antibiotics to reduce the potential for infection and to promote healing, and growth factors to promote bone and/or soft tissue ingrowth into exterior surface 119 of sleeve 110.

Referring again to the illustrative embodiment of prosthesis 100 shown in FIG. 1A, distal stem 130 is shown having proximal end 132, distal end 134, engagement member 136, and beveled member 138. Beveled member 138 is positioned at distal end 134 of distal stem 130 and may comprise one of or both of an anterior and/or posterior bevel, as described in the above-incorporated U.S. patent application Ser. No. 13/025,827.

Distal stem 130 may be circular in cross-section and may taper towards distal end 134 thereby defining a taper angle relative to longitudinal axis 140 or an axis parallel thereto. According to an exemplary embodiment of the present disclosure, the taper angle may be approximately 3.5°. The tapered geometry of distal stem 130 may promote stability of prosthesis 100 in the patient's femur by encouraging distal stem 130 to become wedged into the patient's femoral canal. Also, the tapered geometry of distal stem 130 may evenly distribute axial and bending loads to the patient's femur to resist subsidence and stress shielding. Further, it is within the scope of the present disclosure that distal stem 130 may extend along as little as 55%, 60%, or 65% of the length of prosthesis 100, or along as much as 70%, 75%, or 80% of the length of prosthesis 100, or within any range delimited by any pair of the foregoing values, with proximal body 102 and sleeve 110 extending along the remaining length of prosthesis 100.

Although not illustrated herein, it is also within the scope of the present disclosure that distal stem 130 may include a plurality of longitudinal splines. As depicted and described in the above-incorporated U.S. patent application Ser. No. 13/025,827, each longitudinal spline may project radially outwardly from distal stem 130. Each longitudinal spline may project outwardly from distal stem 130 at a distance of about 0.75 mm, for example. When distal stem 130 is implanted into the patient's femoral canal (FIG. 7A), the longitudinal splines may engage bone that surrounds the canal to provide initial fixation during insertion of prosthesis 100 and to limit rotational movement of prosthesis 100.

Even further, according to exemplary embodiments of the present disclosure, at least a portion of distal stem 130 may be roughened. Similar to embodiments of proximal body 102 described above, distal stem 130 may be plasma sprayed or grit blasted circumferentially to form an outer porous surface. When distal stem 130 is implanted into the patient's femoral canal (FIG. 7A), the porous outer surface may promote bone ingrowth. Additionally, in some embodiments of the present disclosure, distal stem 130 may be constructed of highly porous biomaterial. It is also within the scope of the present disclosure that embodiments of distal stem 130 may include a plurality of longitudinal splines having a porous surface, thereby providing initial fixation of prosthesis 100 and promoting bone ingrowth.

Referring again to the illustrative embodiment of assembled prosthesis 100' shown in FIG. 3, proximal body 102 is shown disposed within cavity 120 of sleeve 110. During assembly, distal portion 108 of proximal body 102 is inserted through proximal opening 122 into cavity 120 of sleeve 110. According to an exemplary embodiment of prosthesis 100, distal portion 108 of proximal body 102 and sleeve 110 may be connected by a Morse type taper-lock arrangement. According to this embodiment, during assembly, a user manipulates proximal body 102 such that distal end 109 of proximal body 102 enters cavity 120 through proximal opening 122 of sleeve 110. The user then forces the externally tapered distal portion 108 of proximal body 102 into the Morse type taper-lock engagement with the internally tapered body 111 of sleeve 110, thereby locking proximal body 102 within sleeve 110. Although described herein as a Morse type taper-lock arrangement, it is within the scope of the present disclosure that other forms of locking arrangements may be used to secure proximal body 102 within sleeve 110, such as fixation screws, threaded arrangements, and locking nuts.

With reference to FIGS. 1A and 6, upon assembly of proximal body 102 within sleeve 110, distal end 109 of proximal body 102 may extend through cavity 120 and out of distal opening 124 of sleeve 110. During assembly, distal end 109 of proximal body 102 couples to engagement member 136 of distal stem 130. In the illustrated embodiment, engagement member 136 is an externally threaded component that screws into internal threads 105 (FIG. 6) of proximal body 102. Additionally, it is within the scope of the present disclosure that engagement member 136 may also comprise a Morse type taper-lock mechanism or fixation screws, for example, for coupling to proximal body 102. Still other embodiments of prosthesis 100 within the scope of the present disclosure may comprise engagement member 136 being directly couplable to sleeve 110, for example to body 111 within cavity 120, in any manner disclosed herein.

Another embodiment of the present disclosure includes proximal body 102 being integrally or monolithically formed with distal stem 130. An integral arrangement of proximal body 102 and distal stem 130 may ensure a strong, stable connection between proximal body 102 and distal stem 130. Also, this integral arrangement may simplify a surgeon's preoperative planning and selection process by requiring only selection of the total length and diameter of prosthesis 100, for example, rather than consideration of the lengths and diameters of proximal body 102 and distal stem 130 individually.

Further, according to some embodiments of the present disclosure, proximal body 102 and distal stem 130 may be connected prior to coupling proximal body 102 and/or distal stem 130 to sleeve 110. In such embodiments, during assembly, proximal body 102 and distal stem 130 are coupled in any manner as disclosed herein. Thereafter, distal end 134 of distal stem 130 is inserted through proximal opening 122 of sleeve 110, thereby extending through cavity 120 and exiting cavity 120 through distal opening 124 of sleeve 110. The user may then lock proximal body 102 and/or distal stem 130 to sleeve 110 in any manner disclosed herein.

It is also within the scope of the present disclosure that the various embodiments, shapes, and sizes of proximal body 102, sleeve 110, and distal stem 130 disclosed herein, may be combined such that desired configurations of prosthesis 100 are possible. For example, an embodiment of prosthesis 100 may include proximal body 102 (FIG. 1B), 102' (FIG. 1C), or 102" (FIG. 1D), combined with sleeve 110 (FIG. 1A) or 110' (FIG. 4), and distal stem 130 including a tapered form with longitudinal splines and a beveled member as described herein. As such, the present disclosure allows surgeons to selectively configure prosthesis 100 to address a patient's specific medical needs such as bending, range of motion, load distribution, and enhanced bone and/or tissue ingrowth with portions of prosthesis 100.

In use, embodiments of prosthesis 100 disclosed herein may be utilized during a femoral prosthesis revision procedure. As part of a femoral prosthesis revision procedure, a surgeon may need to perform an extended trochanteric osteotomy (ETO) procedure which involves temporary removal of at least a portion of the proximal femur, possibly including the greater trochanter, in order to access the originally implanted femoral prosthesis.

Figure 7B:
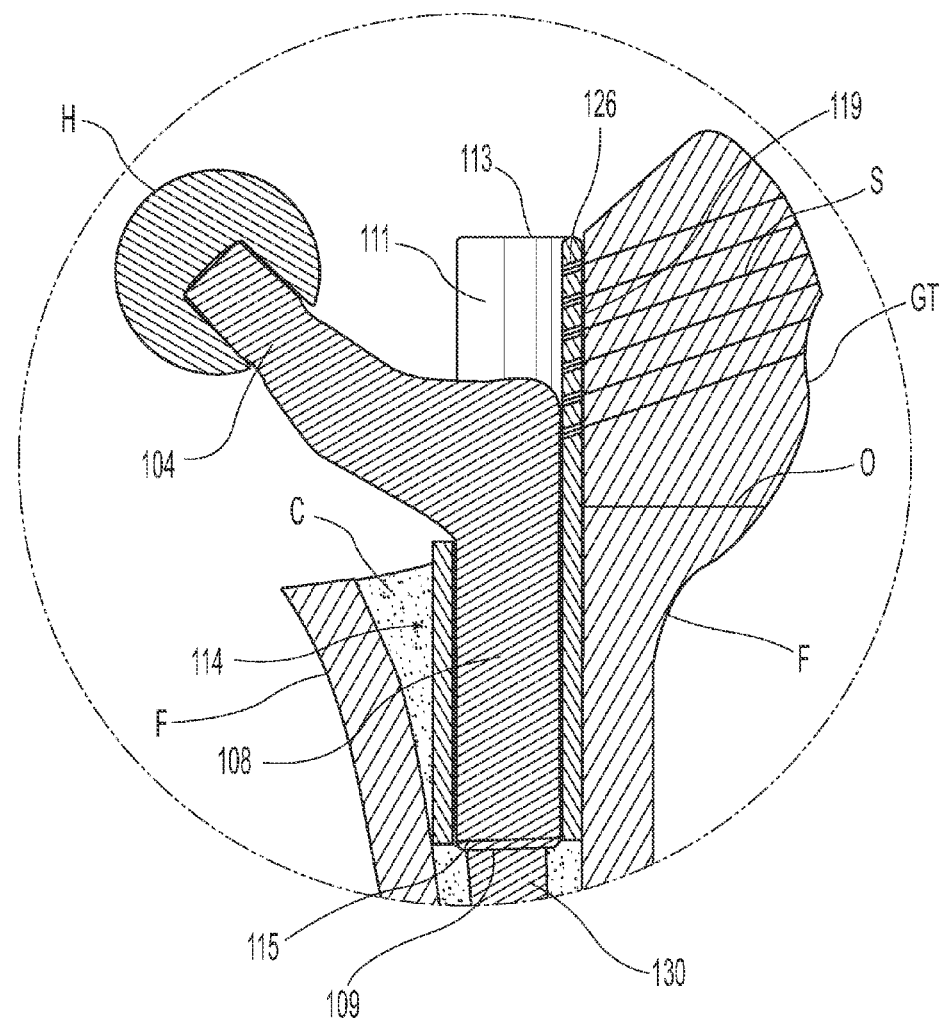
FIG. 7B is a fragmentary view of the proximal portion of FIG. 7A.

Following removal of the originally implanted femoral prosthesis, an assembled prosthesis 100 is implanted into the femoral canal of the patient for replacing the originally implanted femoral prosthesis. Optionally, distal stem 130 of prosthesis 100 may be secured in the femoral canal of patient with bone cement C, or distal stem 130 may be press fitted in femur F without use of bone cement C. The surgeon then reattaches the portion of the proximal femur F temporarily removed during the ETO procedure to exterior surface 119 of the lateral side of sleeve 110 as illustrated in FIG. 7B. For the sake of simplicity and consistency, the portion of the proximal femur F temporarily removed during the ETO procedure is referred to herein as the greater trochanter GT. However, it should be understood that the portion of the proximal femur F temporarily removed during the ETO procedure, and subsequently reattached, may include only a portion of the greater trochanter GT and/or may include additional portions of the proximal femur.

With reference to FIG. 7A, a surgeon may reattach the greater trochanter GT by positioning the greater trochanter GT in contact with exterior surface 119 at the lateral side of proximal region 112 of sleeve 110. At least one surgical fastener S, such as a surgical cable, suture, netting, or tape, may then be threaded through one or more apertures 126 of either anterior or posterior flange 116, 118. For the purpose of simplicity and consistency herein, the surgical fastener S is described as initially coupled to, or threaded through, an aperture 126 of anterior flange 116, although it is within the scope of the present disclosure that the surgical fastener S may initially be coupled to an aperture 126 of posterior flange 118. Remaining with the illustrative embodiment shown in FIG. 7A, the surgical fastener S is then positioned around a lateral portion of the greater trochanter GT such that the surgical fastener S secures the greater trochanter GT against exterior surface 119 of sleeve 110. The surgical fastener S may then be threaded through one or more apertures 126 of posterior flange 118 and may be secured at posterior flange 118. Additional embodiments of the present disclosure include the surgical fastener S being continually threaded from anterior flange 116 to posterior flange 118 for securing the greater trochanter GT against external surface 119 until the surgeon secures the surgical fastener S at one of the flanges 116, 118.

Additional information regarding surgical fasteners and uses thereof for securing tissue to apertures 126 is set forth in U.S. Patent Application Publication No. 2011/0009973, entitled "METHODS AND APPARATUSES FOR ATTACHING TISSUE TO ORTHOPAEDIC IMPLANTS," filed Nov. 13, 2009, assigned to the assignee of the present application, the disclosure of which is hereby expressly incorporated herein by reference.

Referring to FIG. 7B, the surgical fastener S may secure the greater trochanter GT to a proximal portion of exterior surface 119 of sleeve 110, thereby maintaining contact between the greater trochanter GT and exterior surface 119. Maintaining direct contact between the greater trochanter GT and exterior surface 119 in embodiments of prosthesis 100 which include external surface 119 having a porous layer, such as Trabecular Metal™ material or a plasma sprayed porous layer impregnated with biologically active agents, for example, promotes ingrowth of the greater trochanter GT with sleeve 110. Enhanced ingrowth of the greater trochanter GT with the exterior surface 119 of sleeve 110 may aide in preventing the reattached greater trochanter GT from becoming exposed superior to the remainder of the proximal femur F and may aide in preventing loosening of distal stem 130 and/or degradation of the reattached greater trochanter GT.

Figure 8:
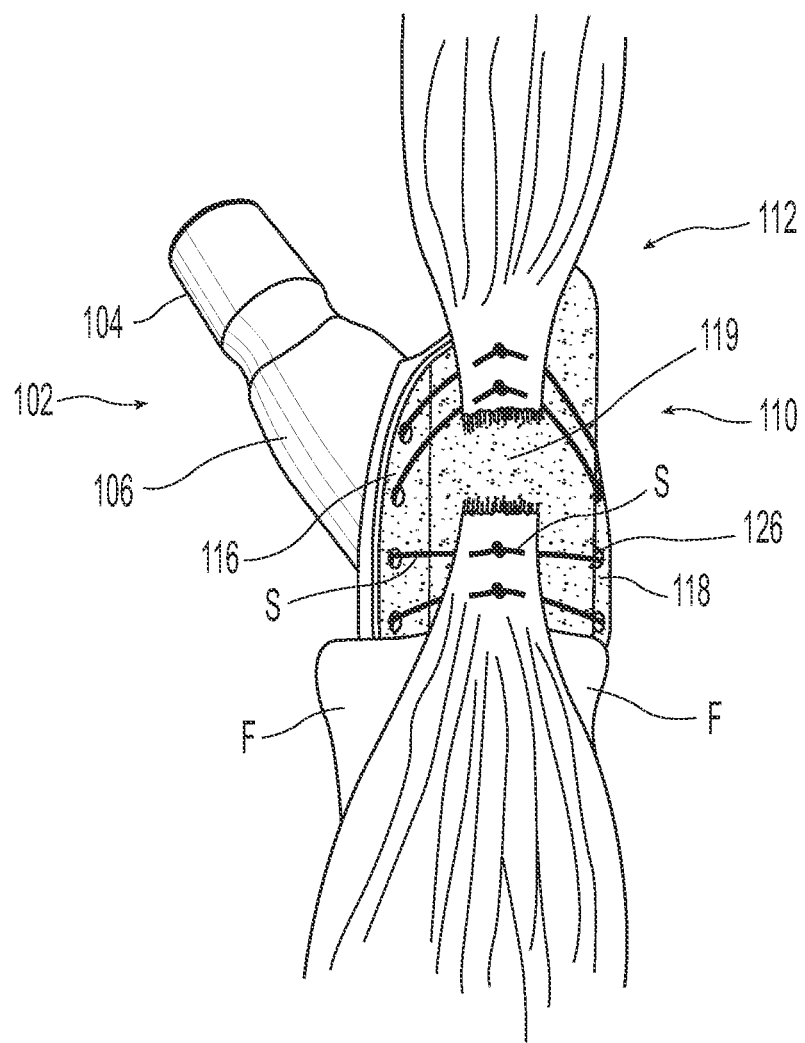
FIG. 8 is an anterior perspective view of an exemplary femoral prosthesis of the present disclosure showing the femoral prosthesis implanted in a femur and soft tissue secured to the sleeve.

Referring to FIG. 8, embodiments of the present disclosure described herein may also include the use of prosthesis 100 when portions of the proximal femur, such as the greater trochanter, must be permanently removed. In such embodiments, portions of sleeve 100, including exterior surface 119, may be used for attachment of soft tissue previously attached to the removed portion(s) of the proximal femur. Embodiments of prosthesis 100 including external surface 119 having a porous layer, as described herein, promote ingrowth of the soft tissue with sleeve 110, thereby facilitating fixation of the soft tissue to sleeve 100 and enhancing soft tissue stability at the joint.

Further, while exemplary embodiments of the present disclosure have described prosthesis 100 for femoral prosthesis revision procedures, it is also within the scope of the present disclosure that prosthesis 100, and its various embodiments described herein, may be used in non-revision procedures. For example, embodiments of prosthesis 100 may be used as a primary femoral prosthesis for implantation into a traumatized hip and/or femur of a patient. Additionally, it is within the scope of the present disclosure that prosthesis 100 may be used as a primary femoral prosthesis when implantation of a femoral prosthesis requires removal of proximal portions of the femur, such as the greater trochanter, which the surgeon wishes to reattach.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A femoral prosthesis having a proximal end and a distal end and configured for implantation in a patient's proximal femur, the femoral prosthesis comprising:
   a proximal body located toward the proximal end of the femoral prosthesis, said proximal body including a proximal portion from which a femoral neck extends;
   a distal stem located at the distal end of the femoral prosthesis; and
   a sleeve coupled to the proximal body and including a plurality of apertures, the sleeve including a lateral exterior surface, at least a portion of the lateral exterior surface positioned proximally of a proximal-most end of said proximal portion of the proximal body.

2. The femoral prosthesis of claim 1, wherein the femoral neck is a modular component coupled to the proximal body.

3. The femoral prosthesis of claim 1, wherein the proximal body extends through a side opening in the sleeve.

4. The femoral prosthesis of claim 1, wherein the lateral exterior surface defines a proximal end of the sleeve, the proximal end of the sleeve extending proximally in a substantially curved manner along a vertical axis, the vertical axis being substantially parallel to the distal stem.

5. The femoral prosthesis of claim 1, wherein the sleeve further comprises a first flange and a second flange, the first flange disposed anteriorly to the second flange, each of the first and second flanges including at least one aperture.

6. The femoral prosthesis of claim 1, wherein the sleeve defines a cavity, the cavity in receipt of at least a distal portion of the proximal body.

7. The femoral prosthesis of claim 6, wherein the distal portion of the proximal body includes a male taper and the cavity of the sleeve includes a corresponding female taper mated to said male taper.

8. The femoral prosthesis of claim 1, wherein a proximal end of the distal stem comprises an engagement member that engages a distal end of the proximal body.

9. The femoral prosthesis of claim 8, wherein the engagement member comprises threads coupled to threads disposed within the proximal body.

10. The femoral prosthesis of claim 6, wherein said sleeve includes
an anterior flange extending longitudinally along the sleeve from said lateral exterior surface, and a posterior flange extending longitudinally along the sleeve from said lateral exterior surface.

11. The femoral prosthesis of claim 10, wherein the cavity includes a distal opening located at a distal-most end of the sleeve.

12. The femoral prosthesis of claim 11, wherein said proximal body and said distal stem are modular components connected together with at least one of said proximal body and said distal stem extending through said distal opening.

13. A femoral prosthesis having a proximal end and a distal end and configured for implantation in a patient's proximal femur, the femoral prosthesis comprising:
a proximal body located toward the proximal end of the femoral prosthesis and incorporating a femoral neck;
a distal stem located at the distal end of the femoral prosthesis; and
a sleeve coupled to the proximal body and including a first flange and a second flange which each extend longitudinally along the sleeve and which each provide a plurality of apertures, said sleeve including a distal region in which a distal wall of the sleeve extends around a full circumference of the sleeve, said sleeve also including a proximal region that provides a side opening through which said proximal body extends.

14. The femoral prosthesis of claim 13, wherein the sleeve includes a cavity defined by the distal region of the sleeve, said cavity including a distal opening at a distal-most end of the sleeve and a proximal opening adjoining said side opening.

15. The femoral prosthesis of claim 14, wherein the proximal body is received in said cavity.

16. The femoral prosthesis of claim 13, wherein the proximal region of said sleeve is comprised of a partial-circumference wall, said partial-circumference wall extending only partially around the proximal region of the sleeve so as to provide said opening opposite said partial-circumference wall.

17. The femoral prosthesis of claim 13, wherein the proximal region of the sleeve includes a proximal wall section that is located proximally of said first flange and said second flange and which provides an additional plurality of apertures.

18. The femoral prosthesis of claim 13, wherein the proximal body includes a proximal portion from which said femoral neck extends, and wherein a proximal region of the sleeve includes a proximal wall section that is positioned proximally of a proximal-most end of said proximal portion of the proximal body.

19. The femoral prosthesis of claim 13, wherein a lateral exterior surface of the sleeve comprises a porous metal.

20. The femoral prosthesis of claim 13, wherein the sleeve defines a cavity, the cavity in receipt of at least a distal portion of the proximal body.

* * * * *